(12) United States Patent
MacLeod et al.

(10) Patent No.: US 8,954,181 B2
(45) Date of Patent: Feb. 10, 2015

(54) SYSTEMS, METHODS, APPARATUSES, AND COMPUTER-READABLE STORAGE MEDIA FOR DESIGNING AND MANUFACTURING CUSTOM DENTAL PREPARATION GUIDES

(75) Inventors: Roddy MacLeod, Charlotte, NC (US); Daniel Michaeli, Long Island City, NY (US); Volker Wedler, Bensheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 235 days.

(21) Appl. No.: 12/961,601

(22) Filed: Dec. 7, 2010

(65) Prior Publication Data

US 2012/0143364 A1  Jun. 7, 2012

(51) Int. Cl.
*G06F 19/00* (2011.01)
*A61C 1/08* (2006.01)
*A61C 13/00* (2006.01)

(52) U.S. Cl.
CPC ............ *A61C 1/082* (2013.01); *A61C 13/0004* (2013.01)
USPC ............. 700/98; 700/182; 700/184; 382/130; 433/72; 433/223

(58) Field of Classification Search
USPC ................................................. 700/98; 703/1
See application file for complete search history.

(56) References Cited

U.S. PATENT DOCUMENTS

| | | | |
|---|---|---|---|
| 4,144,645 A | 3/1979 | Marshall | 32/42 |
| 6,319,006 B1 | 11/2001 | Scherer et al. | 433/512 |
| 6,369,899 B1 | 4/2002 | Hamada | 356/603 |
| 7,044,735 B2 * | 5/2006 | Malin | 433/75 |
| 7,346,417 B2 * | 3/2008 | Luth et al. | 700/117 |
| 7,758,345 B1 * | 7/2010 | Christensen | 433/214 |
| 7,762,814 B2 * | 7/2010 | van der Zel | 433/201.1 |
| 7,801,632 B2 | 9/2010 | Orth et al. | 700/98 |
| 2002/0048741 A1 * | 4/2002 | Jordan et al. | 433/73 |
| 2002/0119432 A1 * | 8/2002 | Ranta et al. | 434/263 |
| 2003/0035107 A1 * | 2/2003 | Overbeck et al. | 356/405 |
| 2004/0151369 A1 | 8/2004 | Schwotzer | 382/154 |
| 2006/0063135 A1 | 3/2006 | Mehl | 433/223 |
| 2006/0093992 A1 * | 5/2006 | Wen | 433/213 |
| 2006/0127848 A1 * | 6/2006 | Sogo et al. | 433/173 |
| 2006/0275737 A1 * | 12/2006 | Kopelman et al. | 433/213 |
| 2007/0154866 A1 * | 7/2007 | Hall | 433/213 |
| 2008/0050700 A1 * | 2/2008 | Weber et al. | 433/202.1 |
| 2008/0085489 A1 * | 4/2008 | Schmitt | 433/75 |
| 2009/0220134 A1 * | 9/2009 | Cahill et al. | 382/128 |

(Continued)

FOREIGN PATENT DOCUMENTS

| | | |
|---|---|---|
| EP | 1 101 451 A2 | 11/2000 |
| JP | 2000-146543 | 5/2000 |
| JP | 2000-292135 | 10/2000 |
| JP | 2002-257528 | 9/2002 |

(Continued)

*Primary Examiner* — Sean Shechtman
(74) *Attorney, Agent, or Firm* — Fitzpatrick, Cella, Harper & Scinto

(57) ABSTRACT

A dental Computer-aided design (CAD)/Computer-aided manufacturing (CAM) system forms a custom dental preparation guide for guiding a dental tool that alters a shapes a tooth structure to which a custom prosthetic dental item is to be attached. The system acquires an optical measurement and an x-ray of at least one dental structure. The system correlates the acquired optical measurement and the x-ray to form a model of the at least one dental structure. The system generates a model of a reduced tooth structure based on the model of the at least one dental structure. The system also provides at least one dental preparation guide based on the model of the reduced tooth structure.

26 Claims, 14 Drawing Sheets

(56) References Cited

U.S. PATENT DOCUMENTS

| | | | |
|---|---|---|---|
| 2010/0151417 A1* | 6/2010 | Nilsson et al. | 433/167 |
| 2010/0196842 A1 | 8/2010 | Jacquemyns | 433/75 |
| 2010/0297574 A1* | 11/2010 | Llop et al. | 433/75 |
| 2011/0066267 A1* | 3/2011 | Schmitt | 700/98 |
| 2011/0196524 A1* | 8/2011 | Giasson et al. | 700/103 |

FOREIGN PATENT DOCUMENTS

| | | |
|---|---|---|
| JP | 2005-172459 | 6/2005 |
| WO | 2007/059780 | 5/2007 |
| WO | WO 2010/086459 A1 | 8/2010 |
| WO | 2013/079437 A2 | 6/2013 |

* cited by examiner

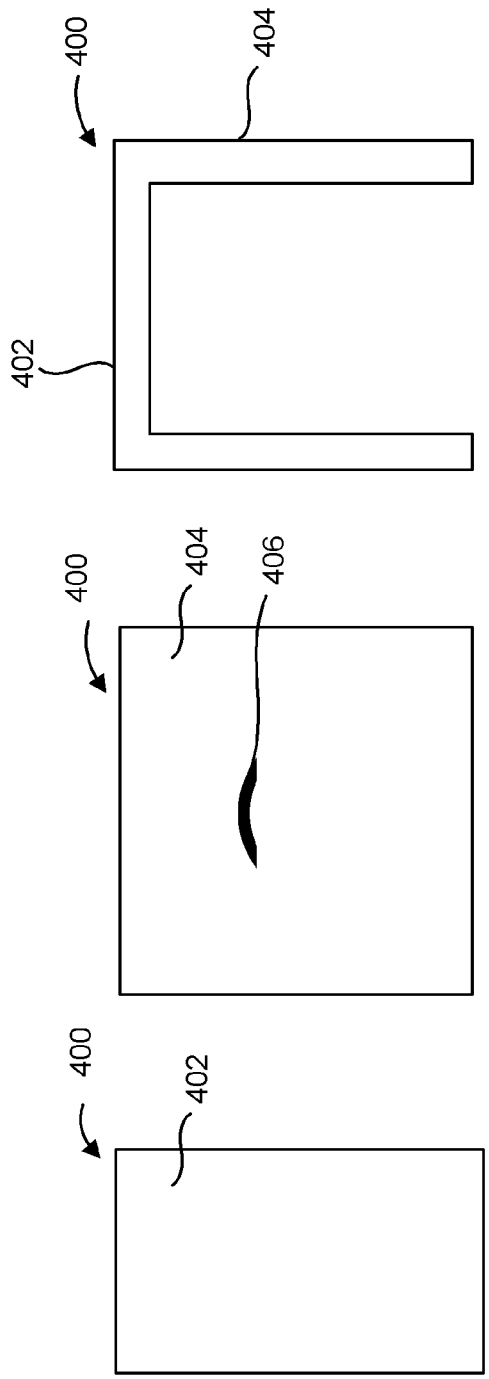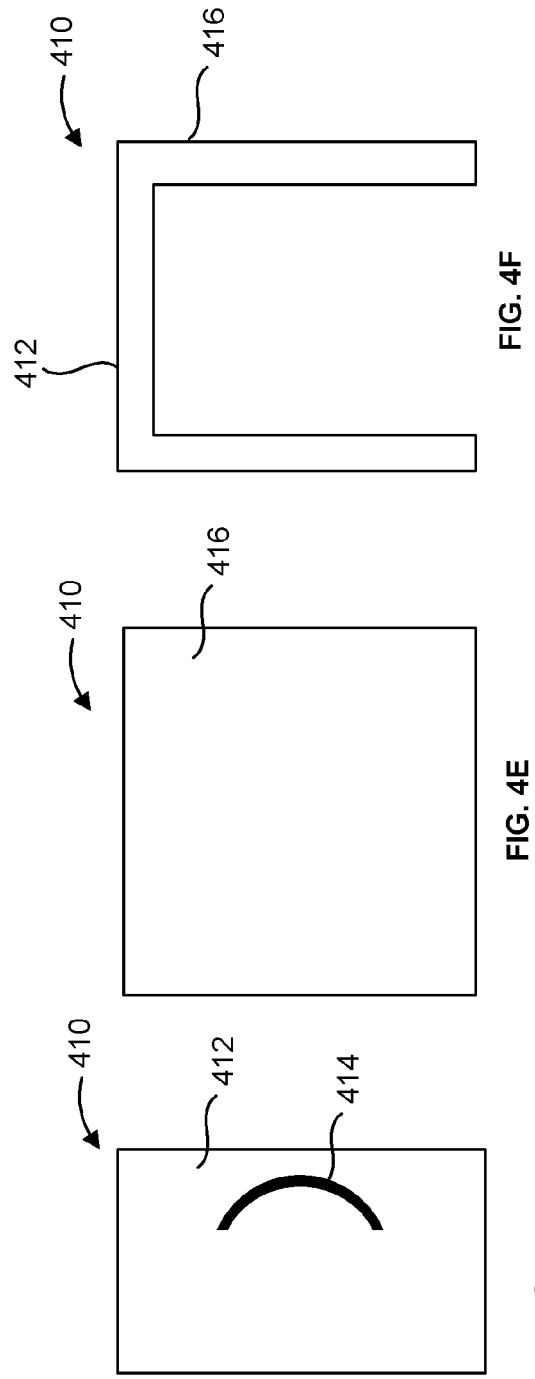

SYSTEMS, METHODS, APPARATUSES, AND COMPUTER-READABLE STORAGE MEDIA FOR DESIGNING AND MANUFACTURING CUSTOM DENTAL PREPARATION GUIDES

BACKGROUND OF THE INVENTION

1. Field of the Invention

The present disclosure relates to computer-aided design and manufacturing, and more particularly to systems, methods, apparatuses, and computer-readable storage media for designing and manufacturing custom dental preparation guides, such as dental drill guides, for prosthetic dental items, such as inlays, onlays, bridges, crowns, and veneers.

2. Description of Related Art

Conventionally, a dental restoration procedure for restoring a damaged tooth has been performed by a dental professional preparing one or more surfaces of the damaged tooth structure (e.g., a tooth stump) by removing tooth decay therefrom, preparing the damaged tooth structure to be attached to the prosthetic dental item by drilling into one or more portions of the damaged tooth structure, and then attaching the prosthetic dental item to the damaged tooth structure. The dental profession can use one or more guides, such as reduction copings, to help ensure that certain portions of the damaged tooth structure are drilled into shapes having predetermined dimensions that are suitable for attaching the prosthetic dental item. For example, a reduction coping can be used to reduce a length of a tooth stump to ensure that, once the prosthetic dental item is attached to the tooth stump, proper clearance between the tooth preparation and occlusion is achieved. Because such guides typically are prepared based upon general guidelines, these guides are not customized for a particular clinical scenario of a particular dental restoration.

Computer-aided design (CAD) and computer-aided manufacturing (CAM) technologies can be employed to design and manufacture customized drill guides that can be superior to conventionally designed and manufactured drill guides. For example, U.S. Pat. No. 6,319,006 discloses a method of producing a drill assistance device for a tooth implant using CAD/CAM technologies.

According to the method disclosed in U.S. Pat. No. 6,319,006, an x-ray picture of a jaw bone is taken and corresponding data is compiled and recorded. Then, three-dimensional, optical measurements of visible surfaces of the jaw bone and attached teeth are performed and corresponding data is compiled and recorded. Data from the x-ray picture is correlated with data from the optical measurements. Using the correlated data, a size and a shape of an implant are planned, a position of the implant relative to adjacent teeth is planned, and a corresponding drill template is produced. The drill template includes a guide hole through which a drill bit of a dental drill can be inserted. After the drill template is attached to teeth adjacent an implant site, a portion of the drill bit is inserted through the guide hole in the drill template, and an implant pilot hole is drilled into the jaw bone at a predetermined location and at a predetermined angle relative to the jaw bone. Using this method, a precise location and orientation of the implant pilot hole in the jaw bone can specified, and the drill template can be used to ensure that the implant pilot hole is drilled at the specified location and at the specified orientation.

The drill template, however, is useful only for guiding the dental drill to drill the implant hole; it is not useful for guiding the dental drill to prepare surfaces of tooth stump for receiving complimentary mating surfaces of a prosthetic dental item. Accordingly, a method of using CAD/CAM technologies to design and manufacture a customized dental preparation guide having a specified connection geometry (e.g., a specified size and a specified shape) for preparing surfaces of a tooth stump is needed.

BRIEF DESCRIPTION OF THE INVENTION

According to an example embodiment herein, a method of forming a custom dental preparation guide includes acquiring an optical measurement of at least one dental structure, acquiring an x-ray of the at least one dental structure, correlating the acquired optical measurement and the x-ray to form a model of the at least one dental structure, generating a model of a reduced tooth structure based on the model of the at least one dental structure, and providing at least one dental preparation guide based on the model of the reduced tooth structure.

According to an example embodiment herein, the model of the tooth structure includes at least one of a neural canal, a tooth contacting surface, and diseased tooth material.

According to an example embodiment herein, the generating includes generating three-dimensional data representing the at least one dental preparation guide.

According to an example embodiment herein, the at least one dental preparation guide includes at least one guide path.

According to an example embodiment herein, the at least one dental preparation guide includes at least one guide path of the dental preparation guide that can guide a dental tool to form a connection geometry in the tooth structure, the connection geometry being for connection of at least one of an inlay, an onlay, a bridge, a crown, and a veneer to the tooth structure.

According to an example embodiment herein, the at least one dental preparation guide if formed using a milling unit.

According to an example embodiment herein, the model of the reduced tooth structure is displayed, and, in response to an instruction to modify the model of the reduced tooth structure the model of the reduced tooth structure is modified during the displaying.

According to an example embodiment herein, a model of a prosthetic dental item to be attached to the reduced tooth structure is generated, and the prosthetic dental item is provided based on the model of the prosthetic dental item.

According to an example embodiment herein, the model of the prosthetic dental item is displayed, and, in response to an instruction to modify the model of the prosthetic dental item, the model of the prosthetic dental item is modified during the displaying.

According to an example embodiment herein, the model of the reduced tooth structure is generated based on the model of the tooth structure and a model of a prosthetic dental item.

According to an example embodiment herein, a system for forming a custom dental preparation guide includes a storage unit storing a program having instructions for fabricating the custom dental preparation guide, and a computer processor operating under control of the program stored in the storage unit. The computer processor operates to: acquire an optical measurement of at least one dental structure, acquire an x-ray of the at least one dental structure, correlate the acquired optical measurement and the x-ray to form a model of the at least one dental structure, generate a model of a reduced tooth structure based on the model of the at least one dental structure, and provide at least one dental preparation guide based on the model of the reduced tooth structure.

According to an example embodiment herein, the model of the tooth structure includes at least one of a neural canal, a tooth contacting surface, and diseased tooth material.

According to an example embodiment herein, the at least one dental preparation guide is an electronic model of the at least one dental preparation guide.

According to an example embodiment herein, the at least one dental preparation guide includes at least one guide path.

According to an example embodiment herein, at least one guide path of the dental preparation guide can guide a dental tool to form a connection geometry in the tooth structure, the connection geometry being for connection of at least one of an inlay, an onlay, a bridge, a crown, and a veneer to the tooth structure.

According to an example embodiment herein, the system further includes a milling unit that forms the at least one dental preparation guide using the model of the at least one dental preparation guide.

According to an example embodiment herein, the system further includes a display unit that displays the model of the reduced tooth structure and, in response to an instruction to modify the model of the reduced tooth structure, the computer processor modifies the model of the reduced tooth structure while the display unit displays the model.

According to an example embodiment herein, the computer processor further operates to generate a model of a prosthetic dental item to be attached to the model of the reduced tooth structure, and provide the prosthetic dental item based on the model of the prosthetic dental item.

According to an example embodiment herein, the system further includes a display unit that displays the model of the prosthetic dental item and, in response to an instruction to modify the model of the prosthetic dental item, the computer processor modifies the model of the prosthetic dental item while the display unit displays the model.

According to an example embodiment herein, the model of the reduced tooth structure is generated based on the model of the tooth structure and a model of a prosthetic dental item.

BRIEF DESCRIPTION OF THE DRAWINGS

FIG. 4A shows a top view of a dental preparation guide according to an example embodiment herein.

FIG. 4B shows a right side view of the dental preparation guide shown in FIG. 4A.

FIG. 4C shows a front side view of the dental preparation guide shown in FIG. 4A.

FIG. 4D shows a top view of a dental preparation guide according to an example embodiment herein.

FIG. 4E shows a right side view of the dental preparation guide shown in FIG. 4D.

FIG. 4F shows a front side view of the dental preparation guide shown in FIG. 4D.

DETAILED DESCRIPTION

Example System Architecture

Example aspects described herein may be implemented using hardware, software, or a combination thereof, and may be implemented in one or more computer systems or other processing systems. Useful machines for performing some or all of the operations described herein include general-purpose digital computers or similar devices.

Figure 1:
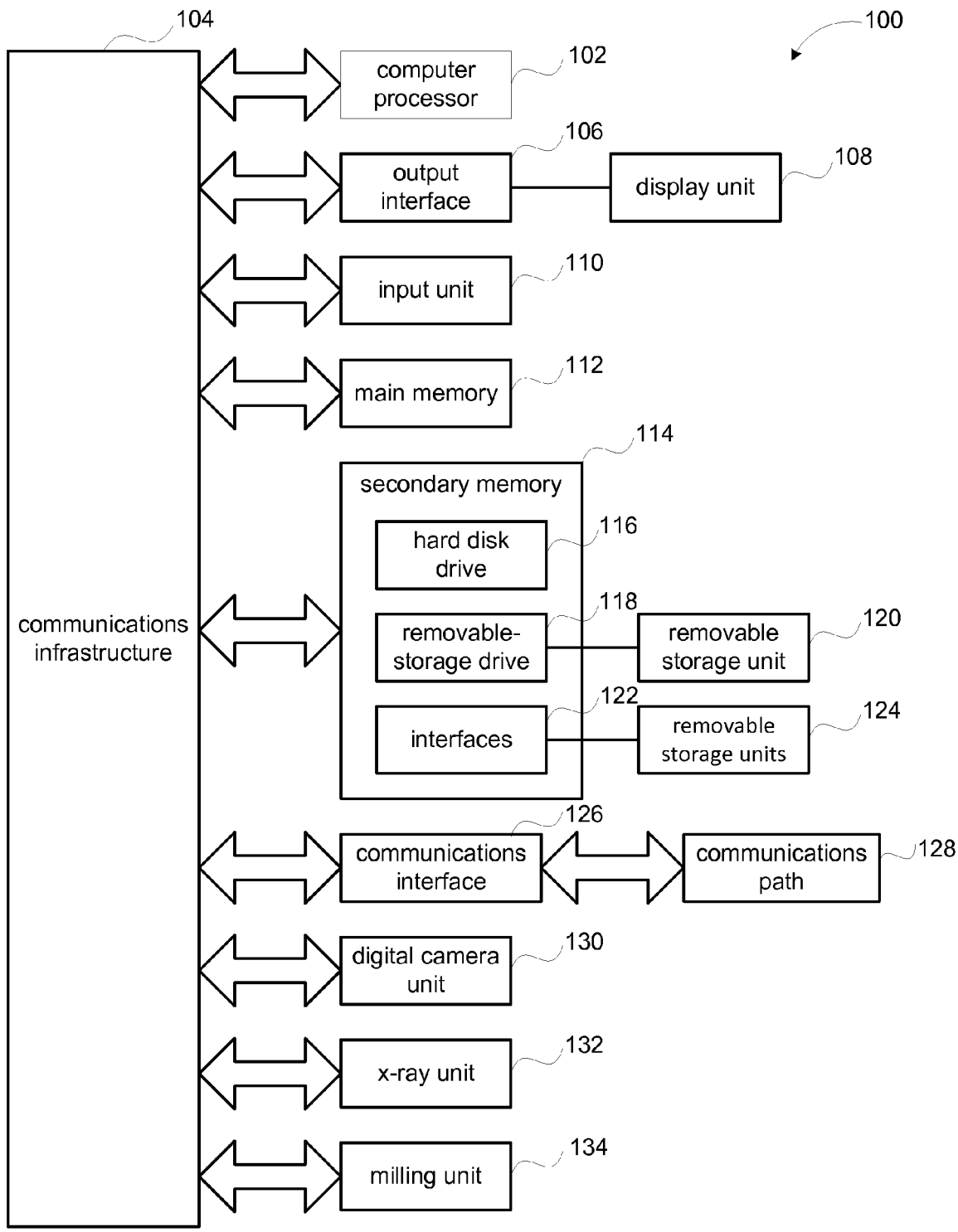
FIG. 1 illustrates a block diagram of a system architecture of a system according to an example embodiment that can perform the process shown in FIG. 2.

In fact, one exemplary embodiment employs one or more computer systems equipped to carry out the functions described herein. An example of such a computer system 100 is shown in FIG. 1.

The computer system 100 includes at least one computer processor 102 (e.g. a central processing unit or a multiple processing unit). The processor 102 is connected to a communication infrastructure 104 (e.g., a communications bus, a cross-over bar device, or a network). Although various software embodiments are described herein in terms of this exemplary computer system 100, after reading this description, it will become apparent to a person skilled in the relevant art(s) how to implement the invention using other computer systems and/or architectures.

The computer system 100 also includes a display interface (or other output interface) 106 that forwards video graphics, text, and other data from the communication infrastructure 104 (or from a frame buffer (not shown)) for display on a display unit 108 (or other output unit).

The computer system 100 also includes an input unit 110 that can be used by a user of the computer system 100 to send information to the computer processor 102. For example, the input unit 110 can include a keyboard device and/or a mouse device or other input device.

In addition, the computer system 100 includes a main memory 112, which preferably is a random access memory ("RAM"), and also may include a secondary memory 114. The secondary memory 114 can include, for example, a hard disk drive 116 and/or a removable-storage drive 118 (e.g., a floppy disk drive, a magnetic tape drive, an optical disk drive, a flash memory drive, and the like). The removable-storage drive 118 reads from and/or writes to a removable storage unit 120 in a well-known manner. The removable storage unit 120 may be, for example, a floppy disk, a magnetic tape, an optical disk, a flash memory device, and the like, which is written to and read from by the removable-storage drive 118. The removable storage unit 120 can include a computer-usable storage medium having computer software instructions and/or data stored therein.

In alternative embodiments, the secondary memory 114 can include other computer-readable media storing computer-executable programs or other instructions to be loaded into the computer system 100. Such devices can include a removable storage unit 124 and an interface 122 (e.g., a program cartridge and a cartridge interface similar to those used with video game systems); a removable memory chip (e.g., an erasable programmable read-only memory ("EPROM") or a programmable read-only memory ("PROM")) and an associated memory socket; and other removable storage units 124 and interfaces 122 that allow software and data to be transferred from the removable storage unit 124 to the computer system 100.

The computer system 100 also can include a communications interface 126 that enables software and data to be transferred between the computer system 100 and external devices (not shown). Examples of the communications interface 126 can include a modem, a network interface (e.g., an Ethernet card), a communications port (e.g., a Universal Serial Bus ("USB") port or a FIREWIRE® port), a Personal Computer Memory Card International Association ("PCMCIA") interface, and the like. Software and data transferred via the communications interface 126 are in the form of signals, which can be electronic, electromagnetic, optical or another type of signal that is capable of being transmitted and/or received by the communications interface 126. Signals are provided to the communications interface 126 via a communications path 128 (e.g., a channel). The communications path 128 carries signals and can be implemented using wire or cable, fiber optics, a telephone line, a cellular link, a radio-frequency ("RF") link, or the like.

The computer system 100 also can include a digital camera unit 130 that generates data representing images captured by the digital camera unit 130 (see, e.g., Step S204 below). The data generated by the digital camera unit 130 can be processed by the processor 102 and/or stored in the secondary memory 114. For example, the processor 102 can process the data generated by the digital camera unit 130 to produce three-dimensional optical impression data that is used in one or more of the methods described herein. The digital camera unit 130 can include a USB interface for connecting the digital camera unit 130 to the communications infrastructure 104, for example. The digital camera unit 130 also can include a wireless interface (e.g. an IEEE 802.11 wireless Local Area Network (LAN) interface or a Bluetooth interface) for connecting the digital camera unit 130 to the communications infrastructure 104.

The computer system 100 also can include an x-ray unit 132 that generates x-rays and collects energy from the x-rays after the x-rays have passed through a region of a patient's mouth. For example, the x-ray unit 132 can be a cone-beam tomography unit. The x-ray unit 132 can include a USB interface for connecting the x-ray unit 132 to the communications infrastructure 104, for example. The x-ray unit 132 also can include a wireless interface (e.g. an IEEE 802.11 wireless LAN interface or a Bluetooth interface) for connecting the x-ray unit 132 to the communications infrastructure 104.

In addition, the computer system 100 can include a milling unit 134 (which can be computerized or not) that controls a cutting arm to mill a milling block based on received instructions. For example, three-dimensional data representing the dental preparation guide 400 can be used to generate a series of instructions for the milling unit 134, which cause the milling unit 134 to mill an acrylic block to form the dental preparation guide 400.

As used herein, the phrases "computer program product," "computer program medium" and "non-transitory computer-readable storage medium" can be used generally to refer to the removable storage unit 120 used with the removable-storage drive 118 or a hard disk installed in the hard disk drive 116, for example. These computer program products provide programs (e.g., software) to the computer system 100. The present invention can be implemented or embodied as one or more of such computer program products.

Computer programs (also referred to as computer control logic) are stored in the main memory 112 and/or the secondary memory 114. The computer programs also can be received via the communications interface 126. Such computer programs include computer-executable instructions which, when executed by the computer processor 102, enable the computer system 100 to perform the procedures as described herein and shown in FIG. 2, for example. Accordingly, such computer programs can control the overall computer system 100.

In an example embodiment described herein implemented using software, the software can be stored in a non-transitory computer-readable storage medium and loaded into the computer system 100 using the removable-storage drive 118, the hard disk drive 116, or the communications interface 126. Control logic (software), when executed by the processor 102, causes processor the 102 to perform the procedures described herein.

In an example embodiment described herein implemented primarily using hardware, for example, hardware components such as application-specific integrated circuits ("ASICs") can be used Implementation of such a hardware arrangement so as to perform the functions described herein will be apparent to persons skilled in the relevant art(s) in view of this description.

Alternatively, example embodiments described herein can be implemented using a combination of both hardware and software.

Example Process

Figure 2:
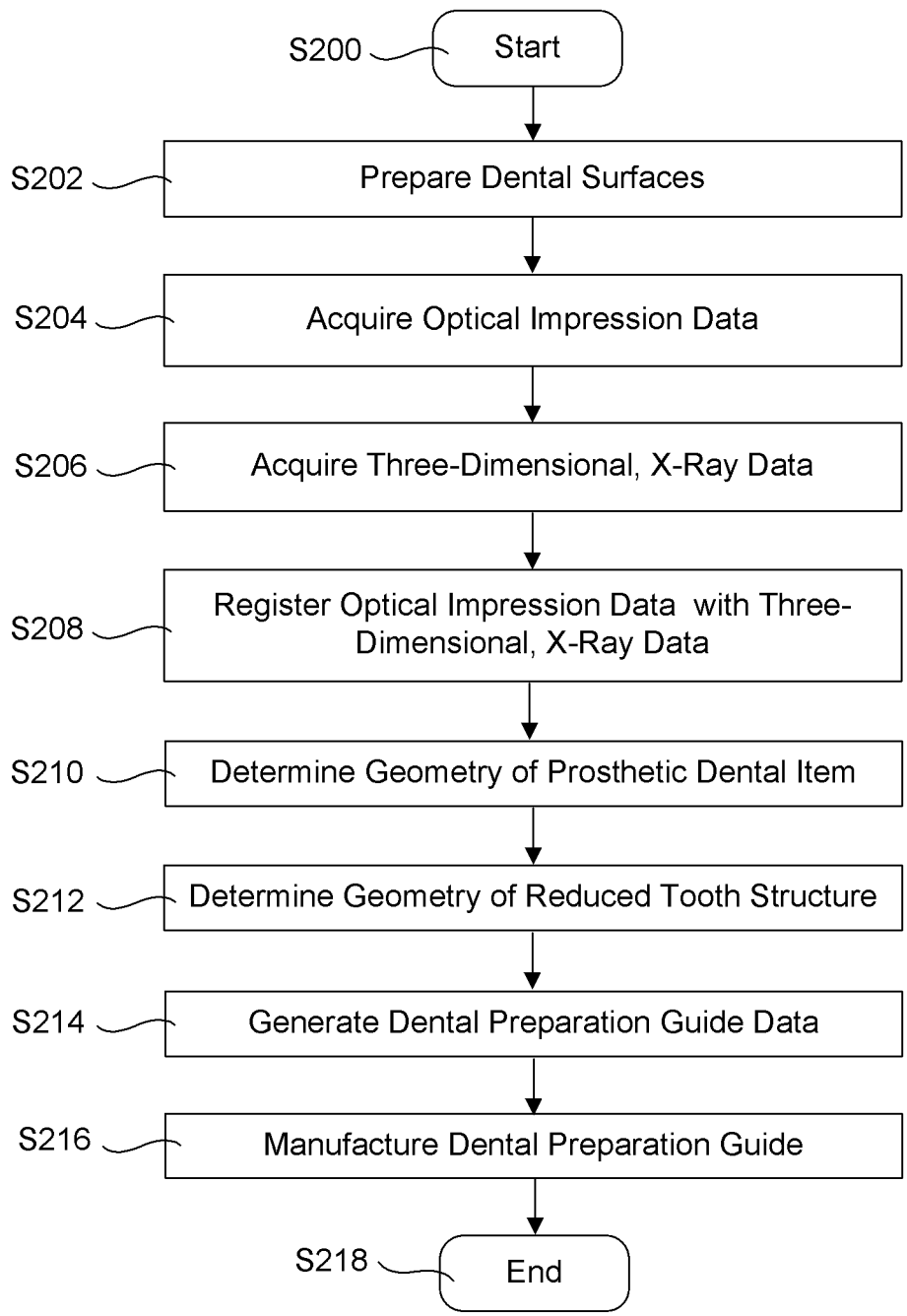
FIG. 2 shows a flow chart of a process for producing a customized dental preparation guide according to an example embodiment herein.

FIG. 2 shows a process of producing a customized dental preparation guide for preparing a damaged tooth structure for receiving a prosthetic dental item according to an example embodiment herein. In one example embodiment, at least part of the process is performed by the system of FIG. 1, as also explained in the description of that figure above. The process beings in Step S200. In Step S202, a dentist or a dental hygienist prepares dental surfaces in the mouth of a patient, for example, by removing decay from surfaces of a damaged tooth structure (e.g., a tooth stump) to which the prosthetic dental item is to be attached.

In Step S204, optical impression data obtained by optically measuring visible surfaces of a dental preparation region that includes the damaged tooth structure is acquired. The optical impression data acquired in Step S204 also can include data obtained by optically measuring visible surfaces of teeth adjacent the damaged tooth structure. For example, the digital camera unit 130 can be inserted into the patient's mouth and a series of images can be captured by the digital camera unit 130, which provides corresponding image data via the communication infrastructure 104 to the computer processor 102, which may process the image data to generate the optical impression data. The optical impression data can be formatted using conventional three-dimensional data formats, for example. The communication infrastructure 104 can receive the image data from the digital camera unit 130 wirelessly or via a cable, for example.

In Step S206, three-dimensional, x-ray data obtained by taking an x-ray picture of the dental preparation region is acquired. The region includes, for example, at least the damaged tooth structure to which the prosthetic dental item is to be attached, and can include adjacent teeth. For example, the x-ray unit 132 can be placed adjacent the patient's mouth and a series of x-ray images can be captured by the x-ray unit 132, which provides corresponding x-ray data via the communication infrastructure 104 to the computer processor 102, which may process the x-ray data. The x-ray data can be formatted using conventional three-dimensional data formats, for example. The communication infrastructure 104 can receive the x-ray data from the x-ray unit 132 wirelessly or via a cable, for example.

Preferably, three-dimensional, cone-beam x-ray data is acquired in Step S206. For example, three-dimensional, cone-beam x-ray data generated by the i-CAT® system produced by Imaging Sciences International, Inc. or generated by the GALILEOS system produced by Sirona Dental Systems, Inc. can be acquired via a wired or wireless communications interface. It is preferable that the x-ray data is from a relatively small region of interest and has a relatively high spatial resolution volume. The x-ray data can include, in one example, data representing a neural canal, tooth contacts, and locations and extents of disease (e.g. carious lesions).

In Step S208, the optical impression data acquired in Step S204 is registered (e.g., correlated) with the three-dimensional, x-ray data acquired in Step S206 to generate composite digital impression data representing the damaged tooth structure. That is, portions of the optical impression data that correspond to a particular portion of the dental preparation region are associated with portions of the three-dimensional, x-ray data that correspond to the same portion of the dental preparation region. For example, a suitable method of registering the optical impression data with the three-dimensional, x-ray data is disclosed at col. 3, line 50, to col. 4, line 16, of U.S. Pat. No. 6,319,006, filed Oct. 31, 2000, by Scherer et al., and entitled "Method for Producing a Drill Assistance Device for a Tooth Implant." The contents of U.S. Pat. No. 6,319,006 are incorporated by reference herein in their entirety. The composite digital impression data representing the damaged tooth structure includes three-dimensional data describing both visible portions of the damaged tooth structure as well as portions of the damaged tooth structure that are obscured by the patient's gums.

In Step S208, the composite digital impression data representing the damaged tooth structure can be analyzed to identify regions that include tooth decay, if any. If any regions that include tooth decay are identified, corresponding portions of the composite digital impression data are demarcated as including decay. A region that includes tooth decay can be identified, for example, by locating a carious lesion in either cross-sectional or isometric views that are generated using three-dimensional x-ray data. Boundaries of the carious lesion may be demarcated by tracing a three-dimensional outline of the carious lesion using a ray-tracing tool, which generates three-dimensional data corresponding to the traced outline of the carious lesion, for example.

In Step S210, the composite digital impression data representing the damaged tooth structure generated in Step S208 is analyzed and three-dimensional data representing the prosthetic dental item (e.g., a crown) to be attached to the damaged tooth structure is generated. In one example, the method described in paragraphs 61-72 of U.S. Patent Application Publication No. 2006/0063135, filed Nov. 10, 2003, by Mehl, and entitled "Method for Producing Denture Parts or for Tooth Restoration Using Electronic Dental Representations," can be used in Step S210 to generate the three-dimensional data representing the prosthetic dental item. The contents of U.S. Patent Application Publication No. 2006/0063135 are incorporated by reference herein in their entirety.

In more detail, and as an example, in Step S210, the three-dimensional data representing the prosthetic dental item can be generated by first calculating an occlusal surface of the prosthetic dental item. As disclosed in U.S. Patent Application Publication No. 2006/0063135, a biogeneric database including predetermined surface data, such as average surface data, can be utilized to suggest a suitable "normal" tooth and corresponding three-dimensional data stored in the database is used for generating the three-dimensional data representing the prosthetic dental item. The biogeneric database can be implemented, at least in part, using the secondary memory 114 shown in FIG. 1, for example.

In addition, in Step S210, surface data from an existing tooth (e.g. a contralateral tooth) can be used in the foregoing generating to generate the three-dimensional data representing the prosthetic dental item. In one example, the method described at col. 3, line 17, to col. 4, line 64, of U.S. Pat. No. 7,801,632, filed Jul. 7, 2005, by Orth et al., and entitled "Method of Designing the Surface of a Dental Prosthetic Item Consisting of Three Dimensional Data," can be used in Step S210 to generate the three-dimensional data representing the prosthetic dental item from surface data of an existing tooth. The contents of U.S. Pat. No. 7,801,632 are incorporated by reference herein in their entirety. (Of course, there are other suitable methods for generating the data in Step S210, besides that in the aforementioned patent.) Additionally, in Step S210, surface data of the damaged tooth to be restored, prior to preparation, can be utilized to generate the three-dimensional data representing the prosthetic dental item. For example, prior to preparation, the damaged tooth can be scanned to generate three-dimensional occlusal surface data of the damaged tooth, which is used as a post-operative structure for the restored tooth.

The three-dimensional data representing the prosthetic dental item can be generated automatically in Step S210. Initially, the composite digital impression data is analyzed, a size of the prosthetic dental item is judged, and tooth structures are scaled. For example, the size of the prosthetic dental item can be determined by calibrating the three-dimensional optical impression and/or x-ray data. Next, the composite digital impression data is analyzed to determine geometries of surfaces of the prosthetic dental item that ensure proper contact with adjacent teeth. A preparation line is then determined. For example, a location of a region of diseased tooth (e.g. a crack or a cavity) can be used to determine a location of the preparation line. Additionally, clinical guidelines regarding an appropriate geometry and shape of a restoration can be used to determine the location of the preparation line.

In addition, in Step S210, after the three-dimensional data representing the prosthetic dental item is generated, structural and/or aesthetic properties of a prosthetic dental item manufactured using this data can be analyzed and/or simulated to determine whether the structural and/or aesthetic properties are acceptable. For example, the three-dimensional data representing the prosthetic dental item and predetermined structural properties of a material (e.g., a ceramic block) from which the prosthetic dental item is to be made can be used to perform a finite element analysis of the structural properties of the prosthetic dental item. Additionally, aesthetic properties of the prosthetic dental item can be simulated using the three-dimensional data representing the prosthetic dental item and information regarding color properties of the material from which the prosthetic dental item is to be formed, for example. In one example embodiment, the method disclosed in paragraphs 30-39 of U.S. patent application Ser. No. 12/625,410 is used to determine the structural properties of the prosthetic dental item and to simulate the aesthetic properties of the prosthetic dental item. The contents of U.S. patent application Ser. No. 12/625,410, filed Nov. 24, 2009, by Schneider et al., and entitled, "Systems, Methods, Apparatuses, and Computer-Readable Storage Media for Designing and Manufacturing Prosthetic Dental Items," are incorporated by reference herein in their entirety.

Figure 3A:
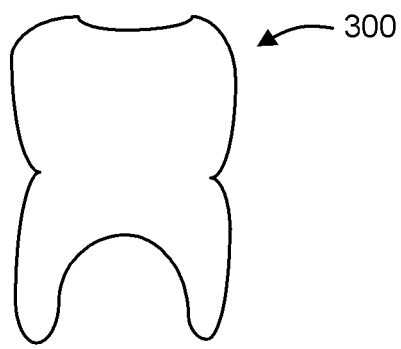
FIG. 3A shows an example of an original tooth.
Figure 3B:
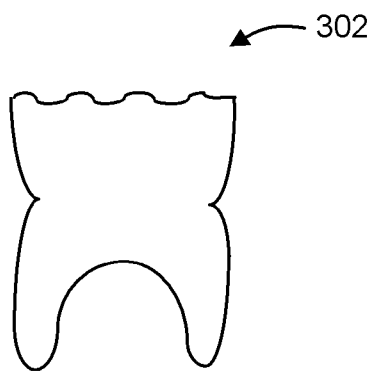
FIG. 3B shows the original tooth shown in FIG. 3A with a top portion thereof removed, which is to be restored using a dental preparation guide according to an example embodiment herein.
Figure 3C:
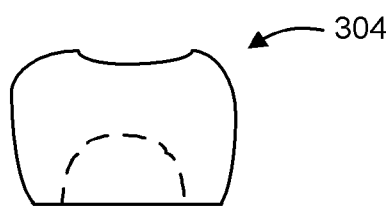
FIG. 3C shows an example of a prosthetic dental item (i.e., a crown) that is to be attached to the tooth shown in FIG. 3B using a dental preparation guide according to an example embodiment herein.

In Step S210, the three-dimensional data representing the prosthetic dental item generated can be used to display a rendering of the prosthetic dental item on a display unit. For example, a Central Processing Unit (CPU) (e.g., computer processor 102) generates three-dimensional data representing a crown 304 and a computer monitor (e.g., display unit 108) displays a rendering of the three-dimensional data representing the crown 304 as shown in FIG. 3C. An operator can review the rendering of the crown 304 and use an input device (e.g., input unit 110) to modify or otherwise manipulate the three-dimensional data representing the crown 304, which causes a rendering of the modified or manipulated three-dimensional data representing the crown 304 to be displayed. More particularly, information input by way of the input device is transmitted to the CPU (e.g., computer processor 102), which generates a corresponding instruction to modify the three-dimensional data representing the crown 304, and execution of that instruction causes the three-dimensional data representing the crown 304 to be modified or manipulated accordingly.

In Step S212, sizes and shapes of surfaces (e.g., a geometry) of a reduced tooth structure to which the prosthetic dental item will be attached are determined. The reduced tooth structure corresponds to a structure of the damaged tooth after portions thereof have been removed by performing a dental preparation procedure. Portions of the damaged tooth structure that include decay should be removed during the dental preparation procedure. The CPU (e.g., computer processor 102) determines a geometry of the reduced tooth structure such that the reduced tooth structure does not include any regions corresponding to portions of the composite digital impression data representing the damaged tooth structure demarcated as including tooth decay in Step S208. For example, the geometry of the reduced tooth structure can be determined by removing regions of diseased tooth, if any, from the damaged tooth structure to produce a remaining tooth structure, and then applying clinical guidelines to the remaining tooth structure to generate data corresponding to the reduced tooth structure such that the reduced tooth structure is capable of supporting the prosthetic dental item (e.g., a crown) and has no stress concentrations, thin margins, etc.

In an example embodiment, in Step S212, the CPU (e.g., computer processor 102) executes software that implements an algorithm to maximize dimensions of the reduced tooth structure, to allow the patient to keep as much of the damaged tooth structure as possible. Dimensions of an interior surface of the prosthetic dental item depend on the dimensions of the reduced tooth structure, as the interior surface of the prosthetic dental item should fit snugly around the reduced tooth structure. In addition, dimensions of an exterior surface of the prosthetic dental item depend on locations and dimensions of adjacent teeth, because the exterior surface of the prosthetic dental should fit between the adjacent teeth. The distance between the interior and exterior surfaces of the prosthetic dental item (i.e., a thickness of the prosthetic dental item) can influence structural properties of the prosthetic dental item.

Initially, in Step S212, the algorithm determines maximum dimensions of the reduced tooth structure such that the reduced tooth structure does not include tooth decay, generates data representing a prosthetic dental item having such dimensions, and performs a structural analysis of the prosthetic dental item using the generated data representing the prosthetic dental item. If the structural properties of the prosthetic dental item are deemed to be acceptable, based on predetermined or operator supplied structural criteria, the maximum dimensions of the reduced tooth structure are deemed to be usable. If the structural properties of the prosthetic dental item are not deemed to be acceptable, the maximum dimensions of the reduced tooth structure are reduced by a predetermined or operator supplied amount, data representing a prosthetic dental item having the reduced dimensions is generated, and a structural analysis of the prosthetic dental item is performed using that generated data. Where the structural properties of the prosthetic dental item are deemed to be acceptable, the current dimensions of the reduced tooth structure are deemed to be usable. If the structural properties of the prosthetic dental item are not deemed to be acceptable, the algorithm is repeated to vary the dimensions again, etc., until a prosthetic dental item is deemed to have acceptable properties, and corresponding dimensions of the reduced tooth structure are identified as being usable.

Once the dimensions of the reduced tooth structure are determined, three-dimensional data representing the reduced tooth structure (e.g. a digital model of the reduced tooth structure) having such dimensions is generated and stored in a computer storage unit (e.g., hard disk drive 116).

In Step S212, the three-dimensional data representing the reduced tooth structure can be used to display a rendering of the reduced tooth structure on a display unit of a computer (e.g., display unit 108). An operator can review the rendering of the reduced tooth structure and use an input device (e.g., input unit 110) to manipulate or modify the three-dimensional data representing the reduced tooth structure, which causes a rendering of the manipulated or modified three-dimensional data representing the reduced tooth structure to be displayed. More particularly, data output by the input device is transmitted to a CPU (e.g., computer processor 102), which causes a corresponding instruction to modify the three-dimensional data representing the reduced tooth structure to be generated and processed, which causes the three-dimensional data representing the reduced tooth structure to be modified accordingly.

In Step S214, sizes and shapes of surfaces of one or more dental preparation guides are determined using the three-dimensional data representing the reduced tooth structure generated in Step S212. For example, the CPU (e.g., computer processor 102) can calculate one or more axial regions and one or more occlusal regions to be removed from the damaged tooth structure, and then generate three-dimensional geometries of dental preparation guides that can be used to remove those regions from the damaged tooth structure. These regions are determined from the three-dimensional, x-ray data generated during a cone-beam x-ray examination, for example. After the extent of the decay is determined, three-dimensional data corresponding to one or more suitable subtractive geometric elements for removing these regions is calculated. The dental preparation guides are designed so as to enable a clinician to drill away the existing decay. Each dental preparation guide includes one or more guide path portions for guiding a dental tool, for example a bit of a dental drill. Of course the guide path portions can be used to guide other dental tools, such as a laser device or a tooth grinding device, for example.

In an example embodiment, the three-dimensional data representing the reduced tooth structure, from Step S112, includes a representation of a top surface (e.g., an occlusal surface) of the reduced tooth structure. Data representing dimensions of a drill bit of a dental drill to be used to remove (i.e., reduce) the top surface of the damaged tooth structure are stored in a computer storage device (e.g., secondary memory 114). In Step S214, the CPU (e.g., computer processor 102) executes a program that implements an algorithm, which uses the three-dimensional data representing the top surface of the reduced tooth structure and the data representing predetermined dimensions of the drill bit of the dental drill to determine corresponding three-dimensional coordinates of a guide path for a dental preparation guide that is to be used to reduce the top surface. That is, the software algorithm generates a representation of the guide path so that, if the drill bit of the predetermined dimensions is placed in the guide path and moved along the surfaces of the guide path, portions of the damaged tooth structure are removed such that the top surface of the resulting tooth structure has the same geometry as the geometry of the top surface of the reduced tooth structure determined in Step S212.

In Step S214, sizes and shapes of surfaces of additional dental preparation guides are selected, if necessary, so that, after all of the dental preparation guides are used in a dental preparation procedure, surfaces of the resulting tooth structure have the same sizes and shapes as the surfaces of the reduced tooth structure determined in Step S212. For example, two dental preparation guides can be used in a dental preparation procedure, wherein one dental preparation guide is for removing an axial portion of the damaged tooth structure and the other dental preparation guide is for removing an occlusal portion of the damaged tooth structure. Once the sizes and shapes of the surfaces of the one or more dental preparation guides are determined, corresponding three-dimensional data representing the one or more dental preparation guides is generated. The three-dimensional data representing the dental preparation guides also includes a representation of one or more guide paths in each dental preparation guide.

In Step S216, the data representing the one or more dental preparation guides generated in Step S214 is transmitted to a milling unit for manufacturing the dental preparation guide. For example, the data representing the one or more dental preparation guides is transmitted via the communication infrastructure 104 to the milling unit 134, and the unit mills the one or more dental preparation guides from one or more acrylic blocks, based on the data representing the one or more dental preparation guides. The process ends in Step S218.

In one embodiment, a plurality of blocks are available, wherein each block includes preparation surfaces having predefined sizes and shapes that are optimized for forming a particular type of dental preparation guide (e.g., a dental preparation guide for occlusal reduction or a dental preparation guide for axial reduction). According to this embodiment, in Step S216, the CPU (e.g., computer processor 102) analyzes data representing the plurality of blocks and data representing a dental preparation guide and selects an optimal one of the plurality of blocks, which the CPU determines can be milled into the dental preparation guide in the fastest amount of time, for example. The CPU provides data identifying the selected block to the milling unit (e.g., milling unit 134). The milling unit uses the data identifying the selected block to acquire the selected block, which the milling unit then uses to form the dental preparation guide.

As will be explained in the detailed example below, the one or more dental preparation guides manufactured in Step S216 can be used to perform one or more dental procedures that cause the damaged tooth to have the geometry (e.g., size and shape) of the reduced tooth structure calculated in Step S212.

Detailed Examples Using the System Architecture and Process Above

A detailed example of how the computer system 100 shown in FIG. 1 can be used to perform the process of producing a customized dental preparation guide shown in FIG. 2 will now be described with reference to FIGS. 3A-3F and 4A-4F. FIG. 3A shows an example of an original tooth 300. FIG. 3B shows a damaged tooth structure 302, which corresponds to the original tooth 300 with a portion thereof removed. For example, the damaged tooth structure 302 results when the portion breaks off the original tooth 300.

A patient having the damaged tooth structure 302 may wish to have a prosthetic dental item attached to the damaged tooth structure 302 to provide a restored tooth having the same characteristics (e.g., size, shape, color properties, structural properties) as the original tooth 300. For example, the patient may visit a dentist's office to have the damaged tooth structure 302 restored by having a crown, which has the same structural properties and appearance as the missing portion of the original tooth 300, attached to the damaged tooth structure 302.

While the patient is in the dentist's office, a dentist prepares dental surfaces (Step S202) of the damaged tooth structure 302, for example, by scraping plaque or dental decay from the dental surfaces of the damaged tooth structure 302. In an example embodiment, prior to performing a dental restoration procedure, optical impression and x-ray examinations are performed to generate three-dimensional data corresponding to a damaged tooth structure, which is used to generate three-dimensional data corresponding to a crown to be attached to the damaged tooth structure, as will be described below. This example embodiment can be particularly useful if all regions of damaged tooth material exist below a patient's gums. Next, the dentist inserts the digital camera unit 130 into the mouth of the patient to acquire optical impression data (Step S204) of a portion the inside of the patient's mouth that includes the damaged tooth structure 302 (e.g., a tooth stump). The dentist then uses the x-ray unit 132 to acquire x-ray data of a portion the patient's mouth that includes the damaged tooth structure 302 (Step S206). For example, the dentist uses the GALLILEOS system from Sirona Dental Systems, Inc. to generate x-ray data and the x-ray data is acquired from the GALLILEOS system. The computer processor 102 then processes the acquired optical measurement data and x-ray data according to known techniques to generate composite digital impression data representing the damaged tooth structure 302 (Step S208).

The computer processor 102 then processes the three-dimensional data representing damaged tooth structure 302 and generates three-dimensional data representing a prosthetic dental item (Step S210) that, once attached to the damaged tooth structure 302, will cause the damaged tooth structure 302 to look like the original tooth 300. For example, the computer processor 102 generates three-dimensional data representing the crown 304 shown in FIG. 3C.

Figure 3D:
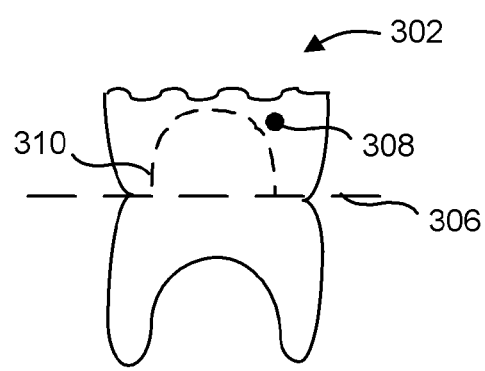
FIG. 3D shows a rendering of three-dimensional data representing the portion of the tooth shown in FIG. 3B according to an example embodiment herein.

The computer processor 102 then processes the three-dimensional data representing damaged tooth structure 302 to identify an appropriate preparation line 306, as shown in FIG. 3D. The preparation line 306 defines a plane on which the prosthetic dental item (e.g., a crown) will sit. The preparation line 306 can be used to define one or more axial regions to be removed from the damaged tooth structure. The computer processor 102 then processes the three-dimensional data representing the damaged tooth structure 302 to identify areas of tooth decay that should not be present in a reduced tooth structure to which the prosthetic dental item is to be attached. For example, assume that a region 308 of the damaged tooth structure 302 is identified in the composite digital impression data representing the damaged tooth structure 302 as including tooth decay, the computer processor 102 generates a reduction geometry 310 that does not include the region 308, as shown in FIG. 3D.

Figure 3E:
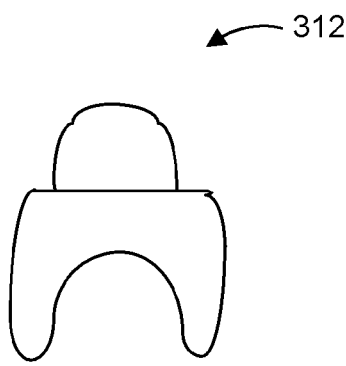
FIG. 3E shows a rendering of three-dimensional data representing a reduced tooth structure that is to be formed using a dental preparation guide according to an example embodiment herein.
Figure 3F:
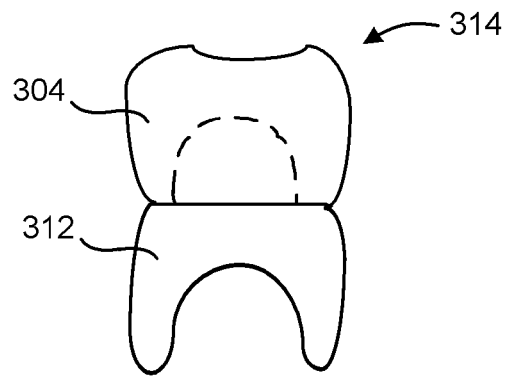
FIG. 3F shows a restored tooth that has been restored using a dental preparation guide according to an example embodiment herein.

The computer processor 102 uses the generated reduction geometry 310 to generate three-dimensional data representing one or more dental preparation guides (Step S214) that can be used to guide a dental tool that is used to shape the damaged tooth structure 302 into a shape of a reduced tooth structure 312, as shown in FIG. 3E.

The computer processor 102 then provides the three-dimensional data representing the one or more dental preparation guides to the milling unit 134, which uses the data to control a cutting blade of a grinding tool or a milling arm to grind or mill the one or more dental preparations guides from one or more blocks of a material, for example a block of an acrylic material (Step S216). For example, the milling unit 134 can use the three-dimensional data generated in Step S214 to form one or more dental preparation guides 400 and 410, as shown in FIGS. 4A-4F.

FIG. 4A shows a top view of dental preparation guide 400 (i.e., as viewed from a perspective looking down thereon). A top side surface 402 of the dental preparation guide 400 is shown in FIG. 4A. FIG. 4B shows a right side view of the dental preparation guide 400 (i.e., a view looking toward a right-facing side of the dental preparation guide 400). A guide path 406 is formed through a portion of a right side surface 404 of the dental preparation guide 400, as shown in FIG. 4B. FIG. 4C shows a front view of the dental preparation guide 400 (i.e., a view looking toward a front-facing side of the dental preparation guide 400). Left side and back side perspectives of the dental preparation guide 400 are not shown in this example, as they are similar to the right and front views, respectively, but on opposite sides. One benefit of designing the crown 304, the reduced tooth structure 312, and the dental preparation guide 400 from the same three-dimensional data, composite digital impression data is that the dimensions of the crown 304 and the reduced tooth structure 312 can be selected to ensure that the restored tooth 314 has proper occlusal properties.

Figure 5:
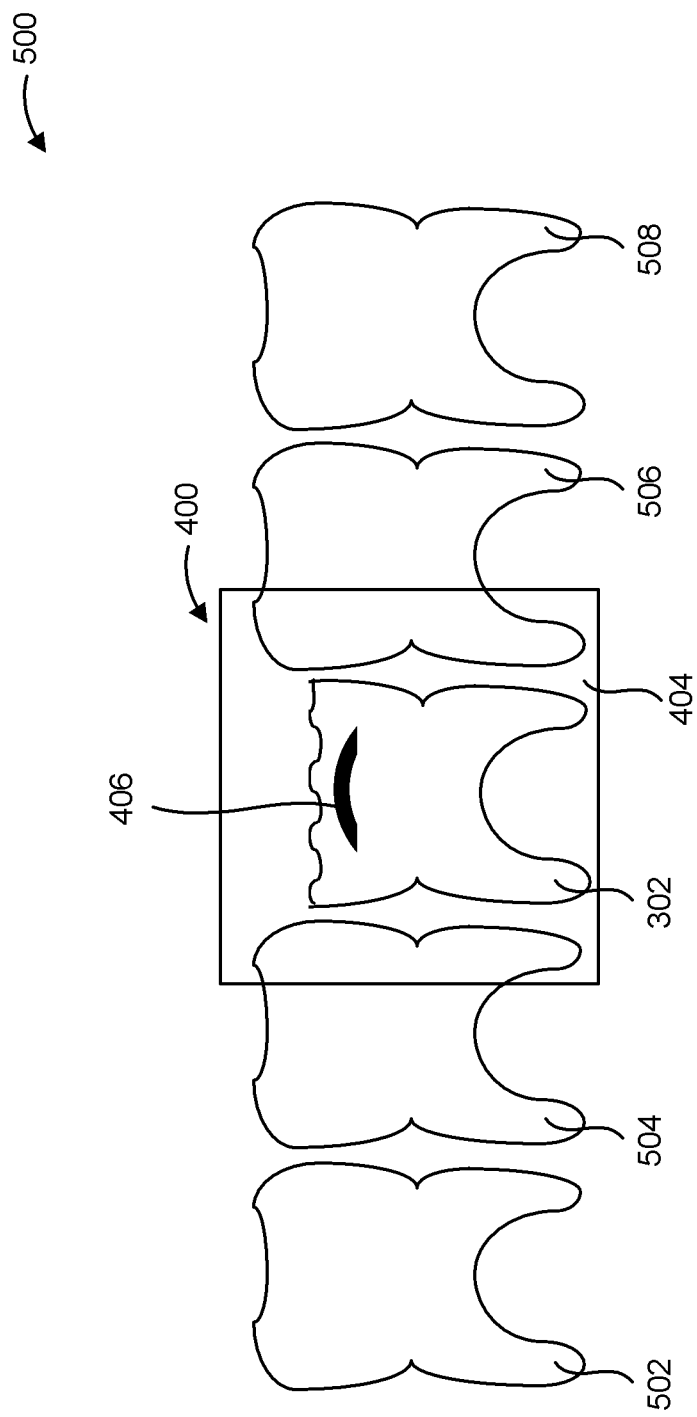
FIG. 5 shows a portion of a patient's mouth with the dental preparation guide shown in FIG. 4A.

FIG. 5 shows a portion of a patient's mouth 500 that includes the damaged tooth structure 302 and adjacent teeth 502-508. The dental preparation guide 400 is secured around the damaged tooth structure 302. For example, lower portions of the top side surface 402 of the dental preparation guide 400 may be contoured to fit to corresponding portions of top surfaces of adjacent teeth 504 and 506, to secure the dental preparation guide 400 around the damaged tooth structure 302. A dental preparation procedure can now be performed wherein a drill bit of a dental drill (not shown) is inserted through the guide path 406 and moved along the guide path 406 from one end of the guide path 406 to the other end, to remove top (e.g. distal) portions of the damaged tooth structure 302. After this is done, the resulting top surface of the damaged tooth structure 302 matches that of the reduced tooth structure 312 shown in FIG. 3E.

FIG. 4D shows a top view of dental preparation guide 410 (i.e., a view from a perspective looking down thereon). A guide path 414 is formed through a portion of a top side surface 412 of the dental preparation guide 410, as shown in FIG. 4D. FIG. 4E shows a right side view of the dental preparation guide 410 (i.e., a view looking toward a right-facing side of the dental preparation guide 410). A right side surface 416 of the dental preparation guide 410 is shown in FIG. 4E. FIG. 4F shows a front view of the dental preparation guide 410 (i.e., a view looking toward a front-facing side of the dental preparation guide 410). Left side and back side perspectives of the dental preparation guide 410 are not shown in this example, as they are similar to the right and front views, respectively, but on opposite sides.

The dental preparation guide 410 can be positioned around the damaged tooth structure 302 and a portion of a dental tool can be inserted through the guide path 414 and moved from one end of the guide path 414 to the other end, to remove axial portions of the damaged tooth structure 302.

Figure 6A:
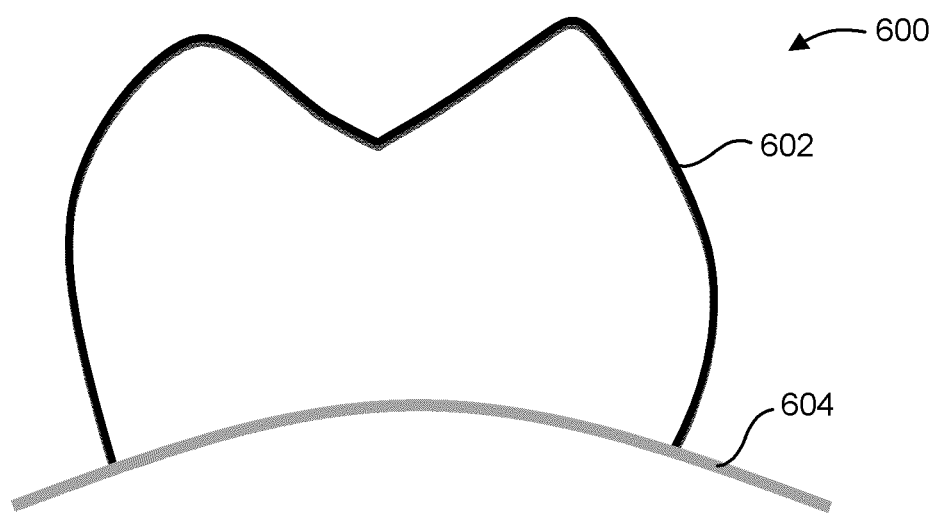
FIG. 6A shows an example of a rendering of a damaged tooth to be restored.

Another detailed example of how the computer system 100 shown in FIG. 1 can be used to perform the process of producing a customized dental preparation guide shown in FIG. 2 will now be described with reference to FIGS. 6A, 6B, and 7A-7H. FIG. 6A shows an example of a rendering of a damaged tooth 600 to be restored. The rendering of the damaged tooth 600 includes a tooth portion 602 and a gum portion 604. The computer system 100 generates three-dimensional data corresponding to the rendering of the tooth portion 602 using composite digital impression data (Step S208) generated by processing acquired optical impression data (Step S204) and x-ray data (Step S206) of a patient's tooth 702.

Figure 6B:
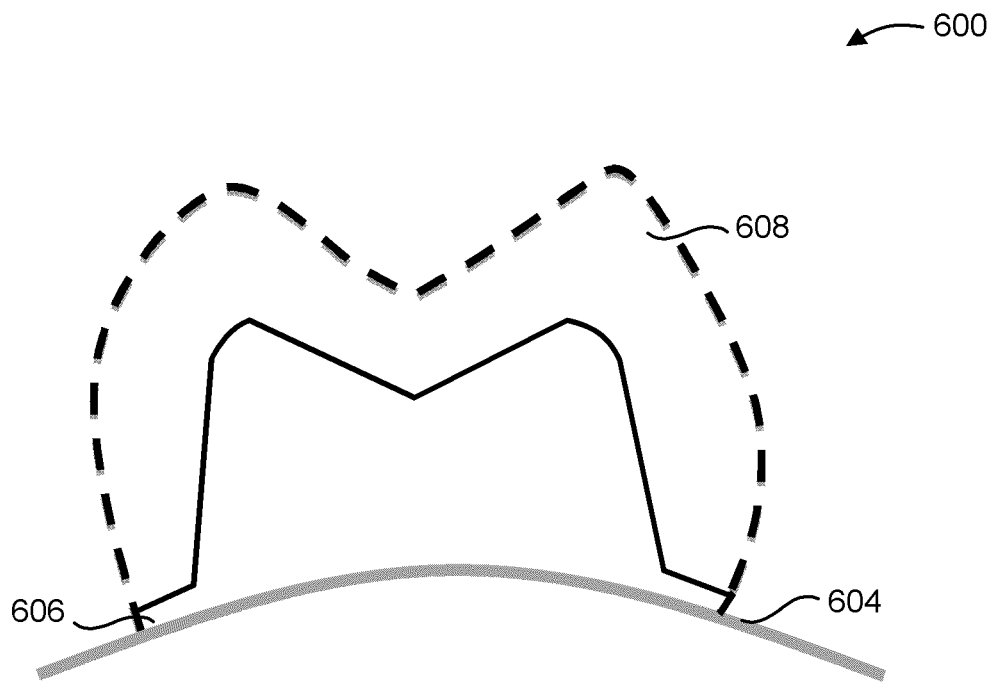
FIG. 6B shows the rendering of the damaged tooth shown in FIG. 6A illustrating a portion to be removed therefrom by a dental preparation procedure.

After determining a geometry of a prosthetic dental item (Step S210) to be attached to the patient's tooth 702, the computer system 100 determines a geometry of a reduced tooth structure (Step S212) to which the prosthetic dental item will be attached after a dental preparation procedure is performed. FIG. 6B shows the rendering of the damaged tooth 600 with a reduced tooth portion 606 having a geometry that corresponds to the geometry of the reduced tooth structure determined in Step S212. FIG. 6B also shows a portion 608 corresponding to a portion to be removed from the patient's tooth 702 by performing the dental preparation procedure. That is, after the portion of the patient's tooth 702 corresponding to the portion 608 is removed, the patient's tooth 702 will have a geometry corresponding that of the reduced tooth portion 606 shown in FIG. 6B.

After the geometry of the reduced tooth structure is determined (Step S212), the computer system 100 generates three-dimensional dental preparation guide data corresponding to two dental preparation guides 708 and 724, to be used during the dental preparation procedure to remove portions of the patient's tooth 702 to cause the tooth 702 to have a structure corresponding to that of the reduced tooth portion 606 shown in FIG. 6B.

Figure 7A:
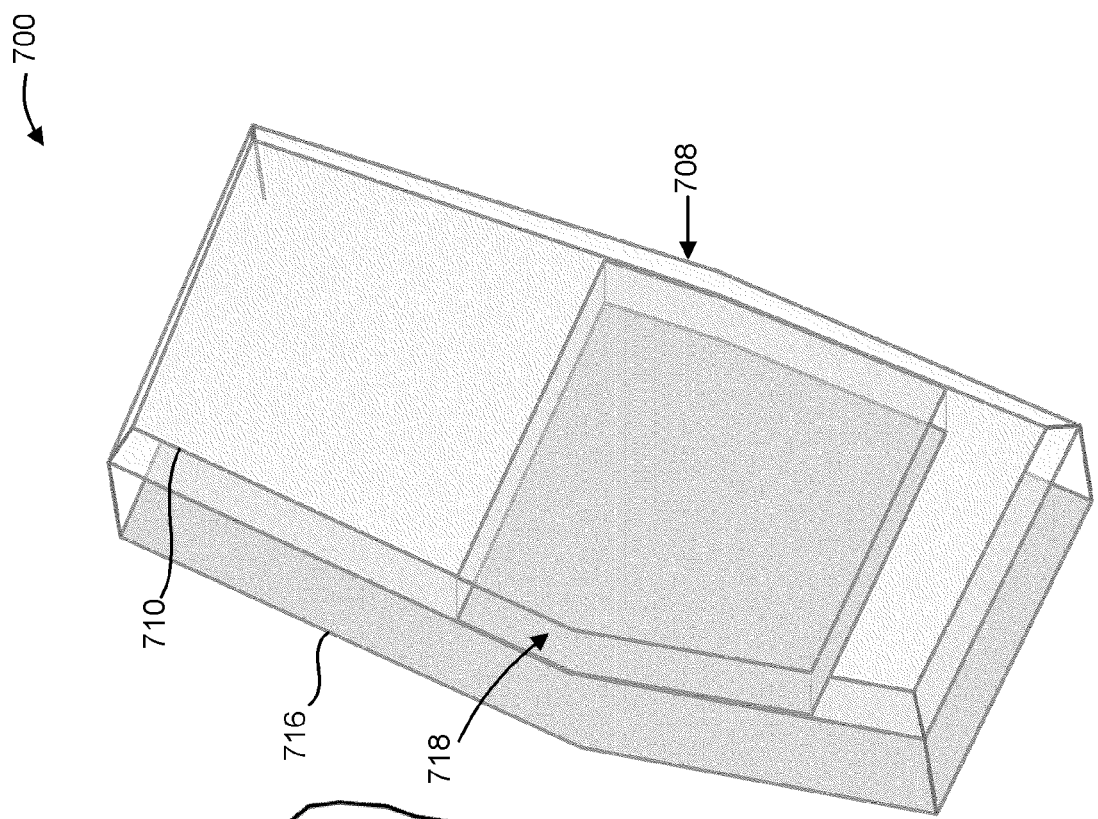
FIG. 7A shows a dental preparation guide according to an example embodiment herein within a portion of a patient's mouth.

FIG. 7A shows a portion of the patient's mouth 700 including the damaged tooth 702, which corresponds to the tooth portion 602 shown in FIG. 6A. The portion of the patient's mouth 700 also includes adjacent teeth 704 and 706 and the dental preparation guide 708. The dental preparation guide 708 includes an upper surface 710, first and second intermediate surfaces 712 and 714 (shown in FIG. 7D), and a bottom surface 716. A guide portion 718 is formed between the first and second intermediate surfaces 712 and 714.

Figure 7B:
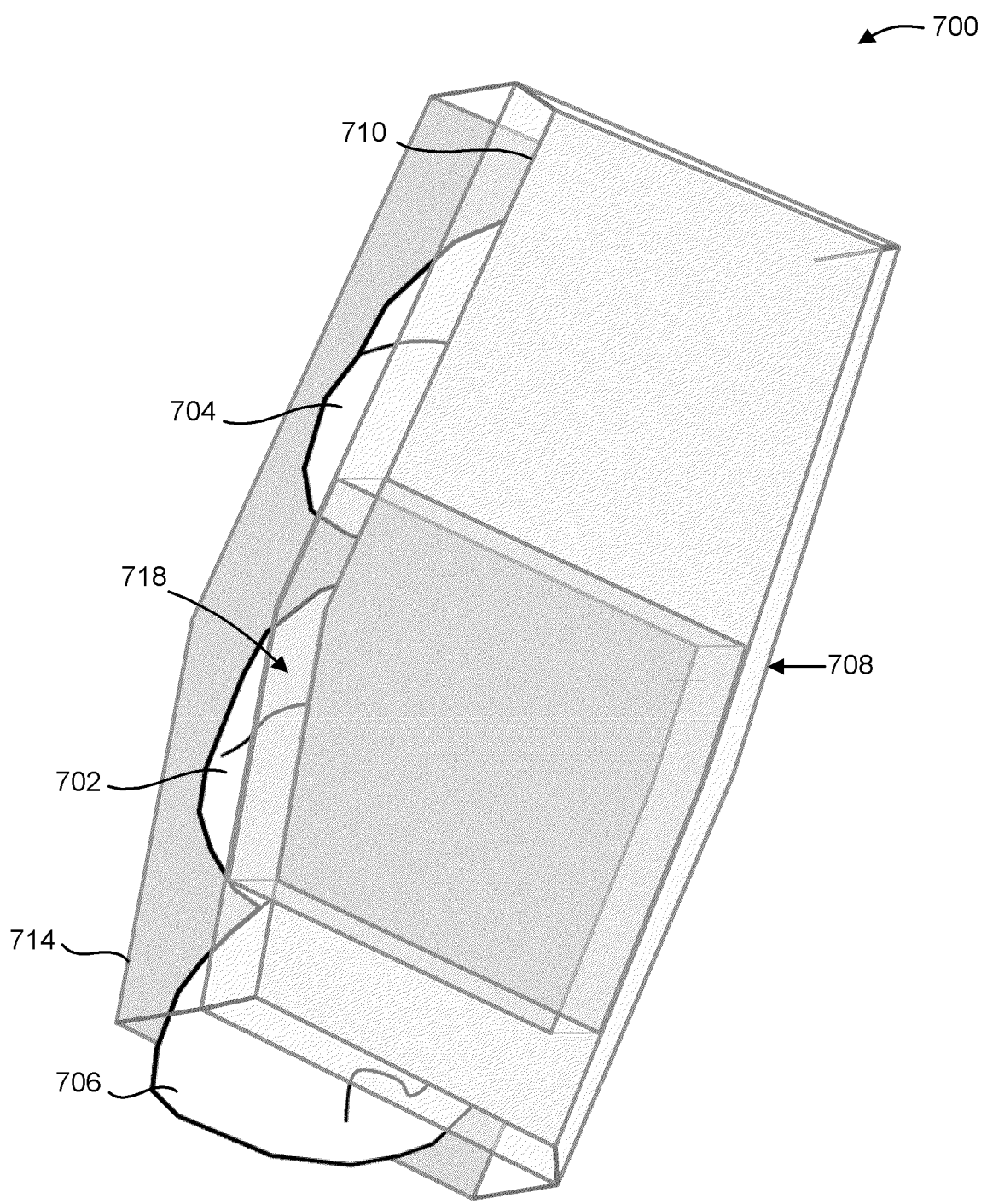
FIG. 7B shows the dental preparation guide shown in FIG. 7A placed over the patient's teeth.
Figure 7C:
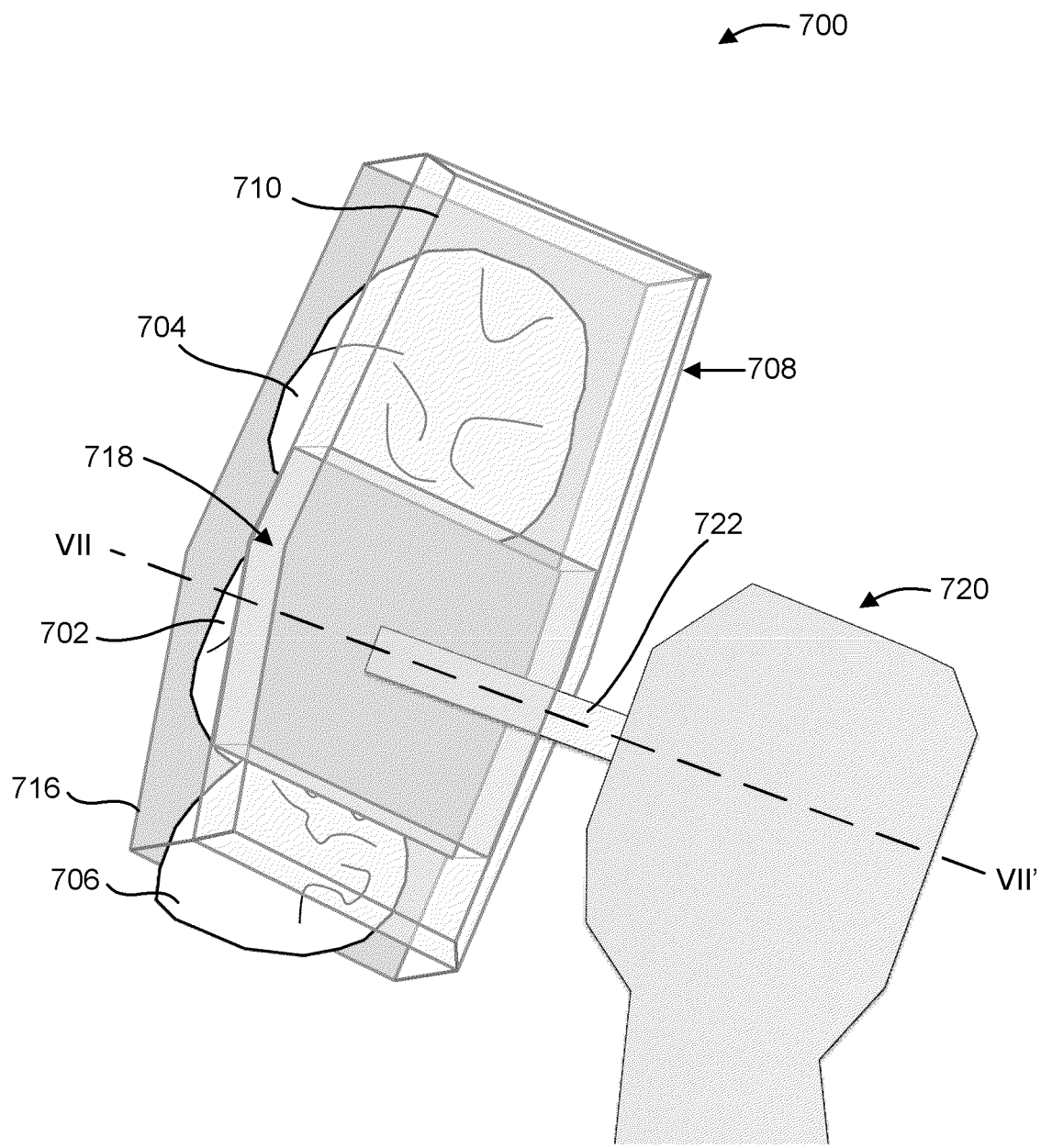
FIG. 7C shows the dental preparation guide shown in FIG. 7B with a portion of a dental tool inserted into a guide portion of the dental preparation guide.
Figure 7D:
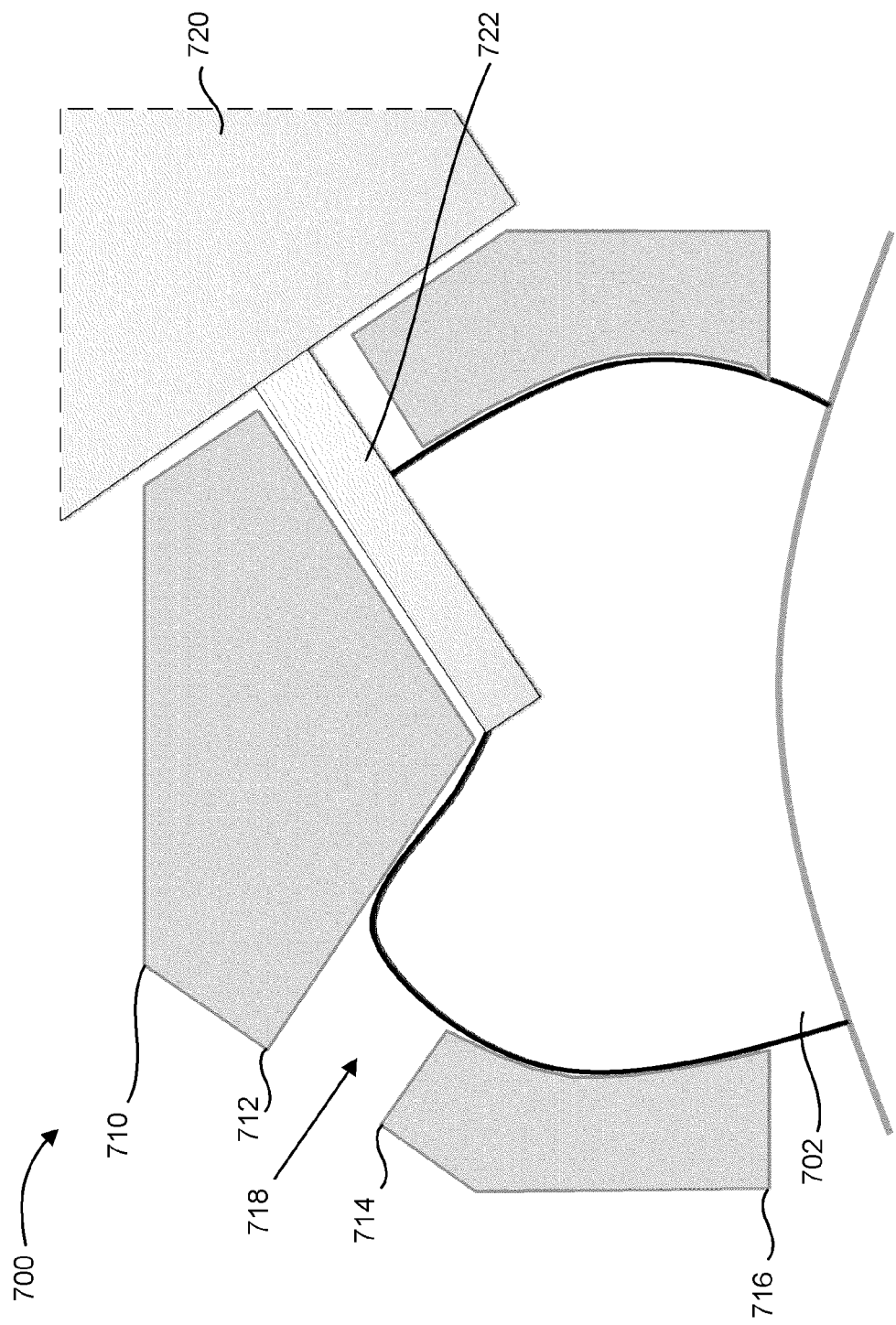
FIG. 7D shows a cross-sectional view of the patient's mouth taken along line segment VII-VII' shown in FIG. 7C.

FIG. 7B shows the dental preparation guide 708 placed over the patient's teeth 702-706. FIG. 7C a portion 722 of a dental tool 720 inserted into the guide portion 718 of the dental preparation guide 708. FIG. 7D shows a cross-sectional view taken along line segment VII-VII' (shown in FIG. 7C). A dental professional moves the portion 722 of the dental tool 720 through the guide portion 718 to remove occlusal portions of the patient's tooth 702. That is, by moving the portion 722 of the dental tool 720 along the guide portion 718, from one end thereof to the other, a top portion of the tooth 702 is removed. The resulting structure of the top portion of the 702 now corresponds to the top portion (not labeled) of the reduced tooth portion 606 shown in FIG. 6B.

Figure 7E:
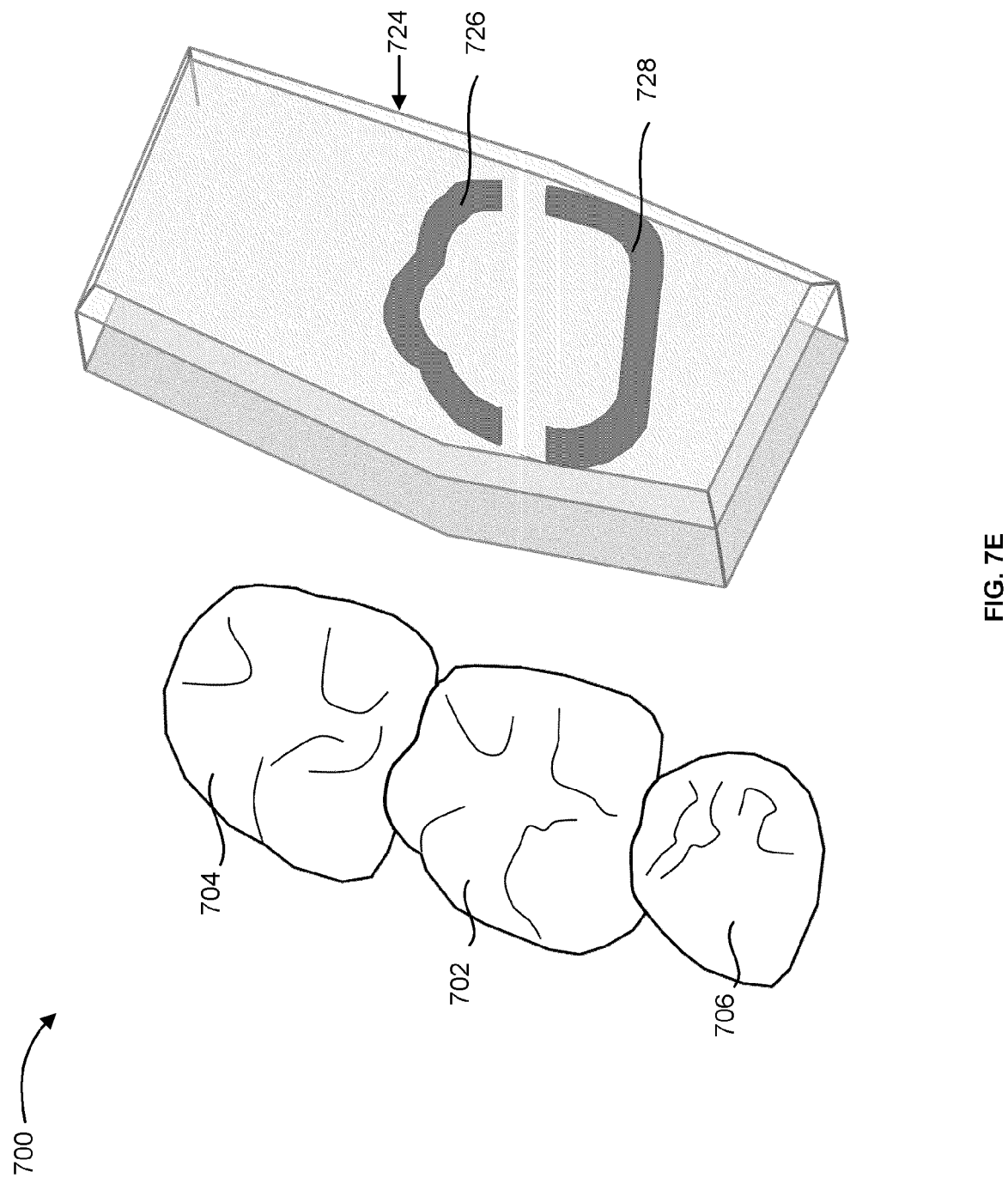
FIG. 7E shows a dental preparation guide according to another example embodiment herein within the portion of the patient's mouth shown in FIG. 7A.

FIG. 7E shows portion of the patient's mouth 700 with the dental preparation guide 724 therein. The dental preparation guide 724 includes guide portions 726 and 728 for guiding the portion 722 of the dental tool 720 to remove axial portions of the patient's tooth 702.

Figure 7F:
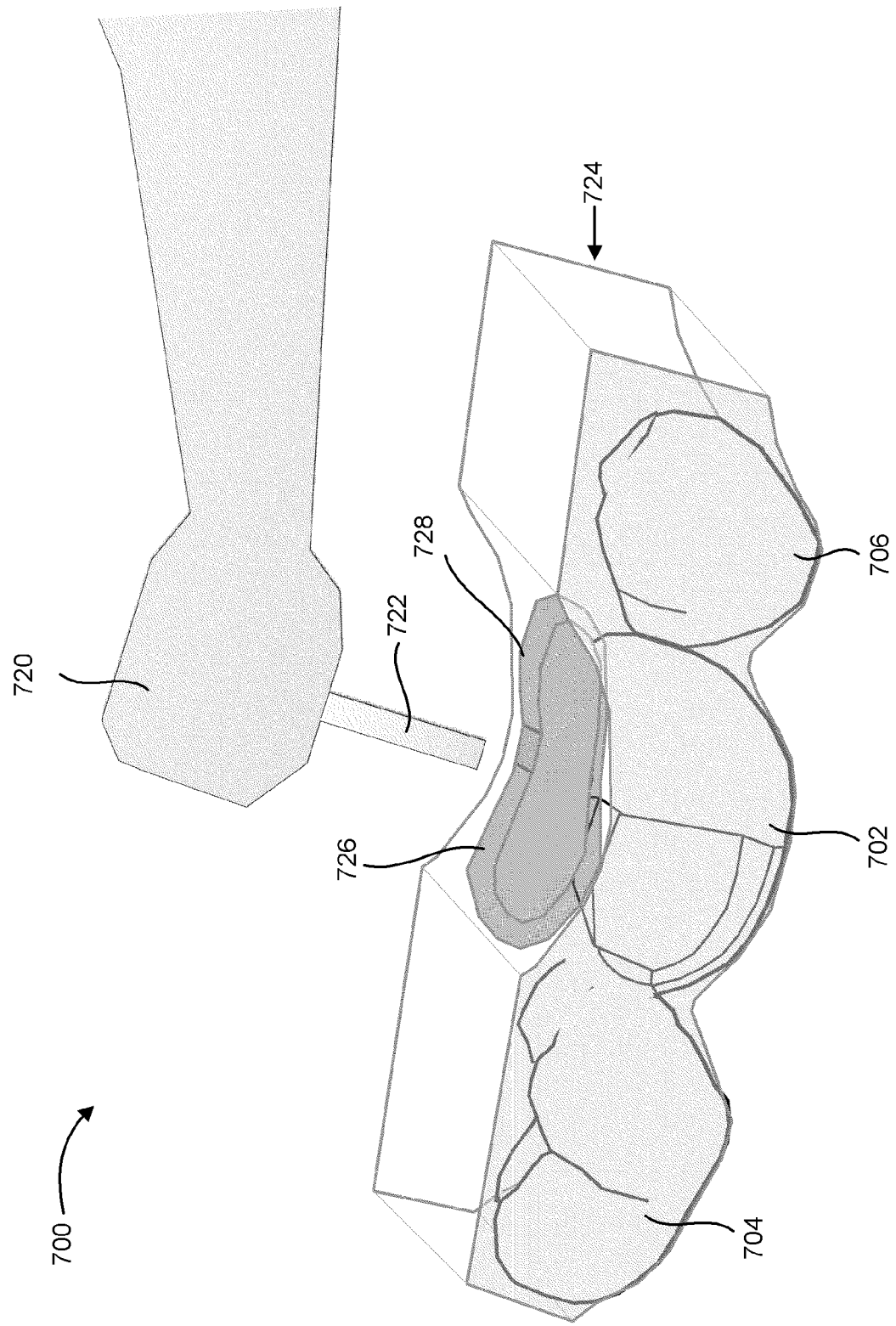
FIG. 7F shows the dental preparation guide shown in FIG. 7E placed over the patient's teeth.
Figure 7G:
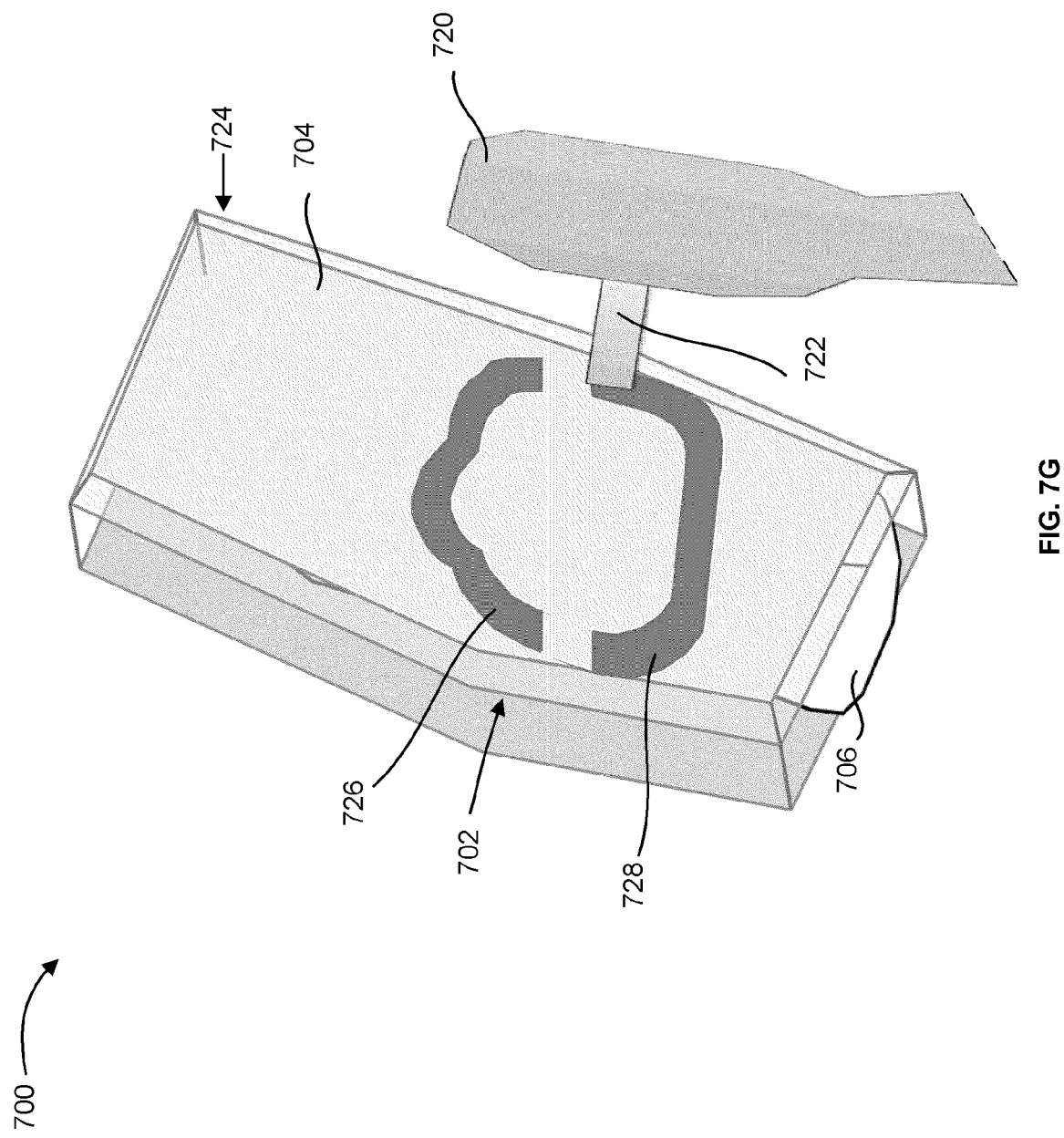
FIG. 7G shows another view of the dental preparation guide shown in FIG. 7F.
Figure 7H:
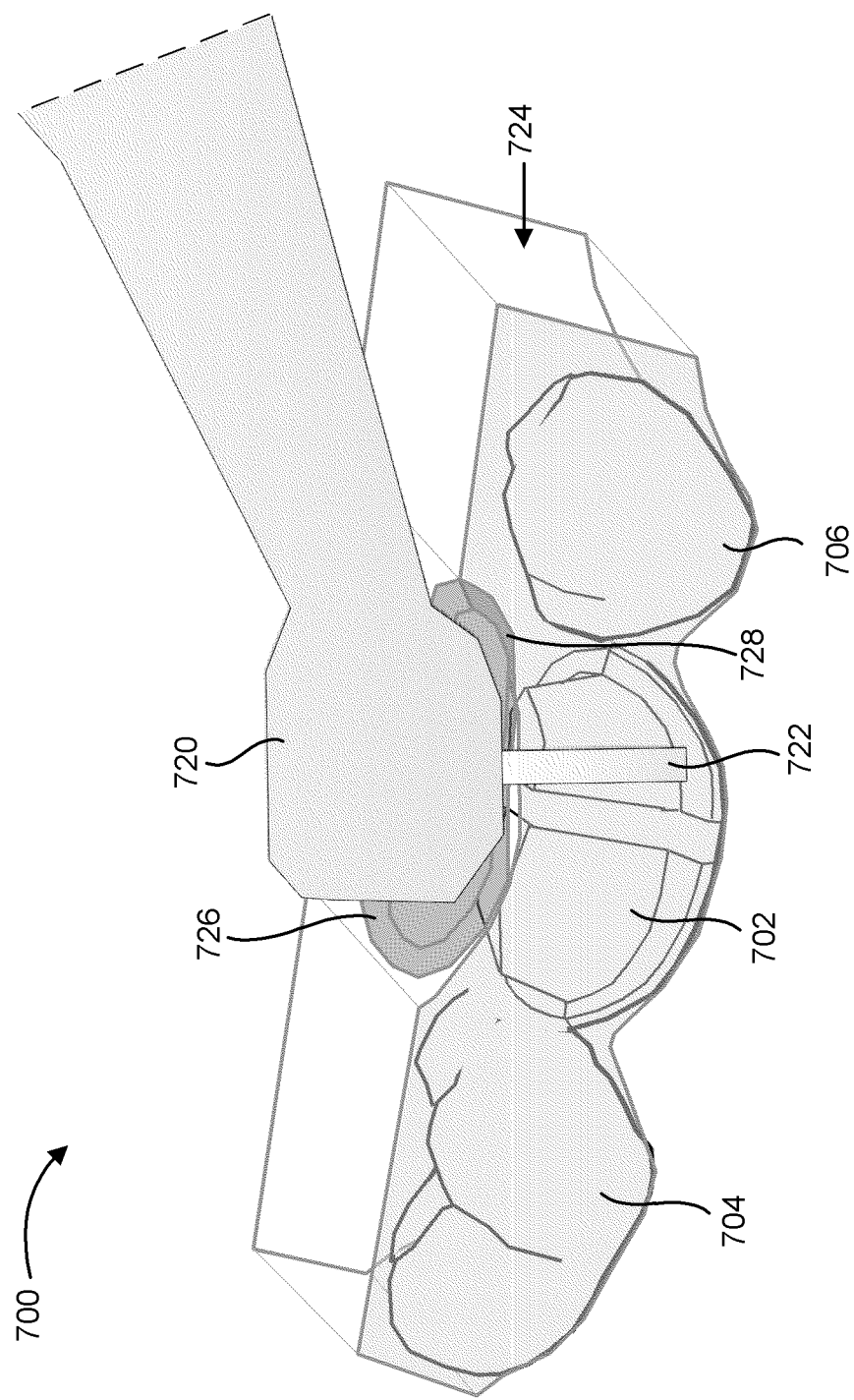
FIG. 7H shows a portion of a dental tool inserted into a guide portion of the dental preparation guide shown in FIG. 7G.

FIG. 7F shows the dental preparation guide 724 placed over the patient's teeth 702-706. FIG. 7F also shows the dental tool 720 placed over the dental preparation guide 724, prior to inserting the portion 722 of dental tool 720 into the guide portions 726 and 728. FIG. 7G shows another view of the dental preparation guide 724 shown in FIG. 7F. FIG. 7H shows the portion 722 of the dental tool 720 inserted into the guide portion 728 of the dental preparation guide 724. The dental professional moves the portion 722 of the dental tool 720 from one end of the guide portion 728 to the other end thereof to remove axial portions of the tooth 702. This process is repeated for the guide portion 726 to remove additional axial portions of the tooth 702. After the axial portions of the tooth 702 have been removed as described above, the resulting structure of the axial portions of the damaged tooth 702 now corresponds to the axial portions (not labeled) of the reduced tooth portion 606 shown in FIG. 6B.

In the foregoing example, the computer system 100 generates three-dimensional data corresponding to two dental preparation guides (i.e., dental preparation guide 708 and 724) for removing occlusal and axial portions of the damaged tooth 702. However, one skilled in the art will readily understand that, the computer system 100 could generate three-dimensional data corresponding to more or less than two dental preparation guides for removing more or less than two portions of the damaged tooth 702. For example, the computer system 100 could generate three-dimensional data in Step S214 that corresponds to five dental preparation guides. In this case, one dental preparation guide could be used to remove an occlusal portion of the damaged tooth 702 and four dental preparation guides could be used to remove four different axial portions of the damaged tooth 702. Each dental preparation guide for removing an axial portion of the damaged tooth 702 could be provided with a guide path corresponding to one quarter of the circumference of the damaged tooth 702, to ensure that tooth material is removed from the entire circumference of the damaged tooth 702. Of course, a selected or desired number of dental preparation guides for removing any number of portions of the damaged tooth 702 can be designed and manufactured to produce any desired connection geometries in the damaged tooth structure 702.

As will be appreciated by those of skill in the relevant art(s) in view of this description, the example aspects described herein can be implemented using a single computer or using a computer system that includes multiple computers each programmed with control logic to perform various of the above-described functions.

The various embodiments described above have been presented by way of example and not limitation. It will be apparent to persons skilled in the relevant art(s) that various changes in form and detail can be made therein (e.g., different hardware, communications protocols, and the like) without departing from the spirit and scope of the present invention. Thus, the present invention should not be limited by any of the above-described exemplary embodiments, but should be defined only in accordance with the following claims and their equivalents.

The foregoing description has been described in the context of example embodiments in which three-dimensional data representing a damaged tooth structure is analyzed to determine a structure of a prosthetic dental item and corresponding dental preparation guides for preparing the damaged tooth structure to be attached to the prosthetic dental item. However, the present disclosure and invention are not limited to that functionality only. Indeed, it also is within the scope of the invention to form a plurality of dental preparation guides for a plurality of prosthetic dental items that are used in combination to restore the damaged tooth structure. One skilled in the art will appreciate, in view of the present disclosure, how to adapt the various steps of the method(s) described above, if at all, to design, evaluate, and form dental preparation guides that can be used for attaching to teeth of animals to receive prosthetic dental items.

In addition, it should be understood that the attached drawings, which highlight functionality described herein, are presented as illustrative examples. The architecture of the present invention is sufficiently flexible and configurable, such that it can be utilized (and navigated) in ways other than that shown in the drawings.

Moreover, the example embodiments described herein are not limited to analyzing and/or simulating dental preparation guides. The example embodiments described herein can be used to analyze and/or simulate virtually any type of preparation guide that can be formed from a block of a material. Moreover, although described herein in the context of an operator performing certain functions of the procedures herein, it should be understood that in other example, the procedures can be performed completely automatically, without operator input.

Further, the purpose of the appended Abstract is to enable the U.S. Patent and Trademark Office and the public generally, and especially scientists, engineers, and practitioners in the relevant art(s), who are not familiar with patent or legal terms and/or phraseology, to determine quickly from a cursory inspection the nature and essence of the technical subject matter disclosed herein. The Abstract is not intended to be limiting as to the scope of the present invention in any way.

What is claimed is:
1. A method of forming a custom dental preparation guide, the method comprising:
    acquiring an optical measurement of at least one dental structure;
    acquiring an x-ray of the at least one dental structure;
    correlating the acquired optical measurement and the x-ray to form a model of the at least one dental structure;

generating a model of a reduced tooth structure based on the model of the at least one dental structure, the model of the reduced tooth structure representing a reduced version of the model of the at least one dental structure remaining after removal of damaged portions thereof; and providing at least one dental preparation guide based on the model of the reduced tooth structure, the dental preparation guide having at least one three-dimensional guide path shaped to receive a tool used to modify at least part of the at least one dental structure.

2. The method of claim 1, wherein the x-ray includes at least one of a neural canal, a tooth contacting surface, and diseased tooth material.

3. The method of claim 1, wherein the providing provides the at least one dental preparation guide in a three-dimensional data format.

4. The method of claim 1, wherein the tool is represented by data.

5. The method of claim 4, wherein the at least one three-dimensional guide path of the dental preparation guide can guide a dental tool to form a connection geometry in the at least one dental structure, the connection geometry being for connection of at least one of an inlay, an onlay, a bridge, a crown, and a veneer.

6. The method of claim 1, wherein the providing includes forming the at least one dental preparation guide using a milling unit or a grinding unit.

7. The method of claim 1, further comprising:
displaying the model of the reduced tooth structure; and
modifying the model of the reduced tooth structure during the displaying, in response to an instruction to modify the model of the reduced tooth structure.

8. The method of claim 1, further comprising:
generating a model of a prosthetic dental item to be attached to the reduced tooth structure; and
providing the prosthetic dental item based on the model of the prosthetic dental item.

9. The method of claim 8, further comprising:
displaying the model of the prosthetic dental item; and
modifying the model of the prosthetic dental item during the displaying, in response to an instruction to modify the model of the prosthetic dental item.

10. The method of claim 8, wherein the model of the reduced tooth structure is generated based on the model of the at least one dental structure and the model of the prosthetic dental item.

11. The method of claim 3, further comprising forming at least one structural dental preparation guide, based on the providing.

12. The method of claim 11, further comprising modifying at least part of the at least one dental structure by way of the at least one three-dimensional guide path to provide a modified version of the at least one dental structure, wherein at least part of the modified version of the at least one dental structure has a geometry that is substantially the same as a geometry of the model of the reduced tooth structure.

13. The method of claim 12, further comprising determining the geometry of the model of the reduced tooth structure.

14. The method of claim 1, wherein the tool is used to modify at least part of the at least one dental structure for receiving complimentary mating surfaces of a prosthetic dental item.

15. A system for forming a custom dental preparation guide, the system comprising:
a storage unit storing a program having instructions for fabricating the custom dental preparation guide; and a computer processor operating under control of the program stored in the storage unit, the computer processor operating to:
acquire an optical measurement of at least one dental structure;
acquire an x-ray of the at least one dental structure;
correlate the acquired optical measurement and the x-ray to form a model of the at least one dental structure;
generate a model of a reduced tooth structure based on the model of the at least one dental structure, the model of the reduced tooth structure representing a reduced version of the model of the at least one dental structure remaining after removal of damaged portions thereof; and
provide at least one dental preparation guide based on the model of the reduced tooth structure, the dental preparation guide having at least one three-dimensional guide path shaped to receive a tool used to modify at least part of the at least one dental structure.

16. The system of claim 15, wherein the x-ray includes at least one of a neural canal, a tooth contacting surface, and diseased tooth material.

17. The system of claim 15, wherein the at least one dental preparation guide is an electronic model version of at least one structural dental preparation guide.

18. The system of claim 15, wherein the tool is represented by data.

19. The system of claim 18, wherein the at least one three-dimensional guide path of the dental preparation guide can guide a dental tool to form a connection geometry in the at least one dental structure, the connection geometry being for connection of at least one of an inlay, an onlay, a bridge, a crown, and a veneer.

20. The system of claim 17, further comprising a milling unit that forms at least one structural dental preparation guide using the electronic model version of the at least one structural dental preparation guide.

21. The system of claim 15, further comprising:
a display unit that displays the model of the reduced tooth structure, wherein the computer processor modifies the model of the reduced tooth structure while the display unit displays the model, in response to an instruction to modify the model of the reduced tooth structure.

22. The system of claim 15, wherein the computer processor further operates to:
generate a model of a prosthetic dental item to be attached to the model of the reduced tooth structure; and
provide the prosthetic dental item based on the model of the prosthetic dental item.

23. The system of claim 22, further comprising:
a display unit that displays the model of the prosthetic dental item, wherein the computer processor modifies the model of the prosthetic dental item while the display unit displays the model, in response to an instruction to modify the model of the prosthetic dental item.

24. The system of claim 22, wherein the model of the reduced tooth structure is generated based on the model of the at least one dental structure and the model of the prosthetic dental item.

25. The system of claim 20, wherein the at least one structural dental preparation guide tool includes at least one guide path portion conforming to the at least one three-dimensional guide path, wherein the at least one guide path portion is arranged to enable at least one dental tool to be received therein for modifying the at least one dental structure such that the at least one dental structure has a geometry that is substantially the same as a geometry of the model of the reduced tooth structure.

26. A non-transitory computer-readable medium storing instructions which, when executed by at least one computer processor, cause the at least one computer processor to implement a method for forming a custom dental preparation guide, the method comprising:

acquiring an optical measurement of at least one dental structure;

acquiring an x-ray of the at least one dental structure;

correlating the acquired optical measurement and the x-ray to form a model of the at least one dental structure;

generating a model of a reduced tooth structure based on the model of the at least one dental structure, the model of the reduced tooth structure representing a reduced version of the model of the at least one dental structure remaining after removal of damaged portions thereof; and providing at least one dental preparation guide based on the model of the reduced tooth structure, the dental preparation guide having at least one three-dimensional guide path shaped to receive a tool used to modify at least part of the at least one dental structure.

\* \* \* \* \*